US006706897B1

(12) United States Patent
Brunelle et al.

(10) Patent No.: US 6,706,897 B1
(45) Date of Patent: Mar. 16, 2004

(54) METHOD FOR PREPARING OXYDIPHTHALIC ANHYDRIDES USING GUANIDINIUM SALT AS CATALYST

(75) Inventors: Daniel Joseph Brunelle, Burnt Hills, NY (US); Qing Ye, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/373,430

(22) Filed: Feb. 24, 2003

(51) Int. Cl.[7] ............................................. C07D 307/89
(52) U.S. Cl. ....................................................... 549/241
(58) Field of Search .......................................... 549/241

(56) References Cited

U.S. PATENT DOCUMENTS

| | | |
|---|---|---|
| 4,837,404 A | 6/1989 | Schwartz |
| 4,870,194 A | 9/1989 | Molinaro et al. |
| 4,948,904 A | 8/1990 | Stults |
| 5,021,168 A | 6/1991 | Molinaro et al. |
| 5,116,975 A | 5/1992 | Brunelle |
| 5,132,423 A | 7/1992 | Brunelle et al. |
| 5,153,335 A | 10/1992 | Stults |
| 5,229,482 A | 7/1993 | Brunelle |
| 6,028,203 A | 2/2000 | Brunelle et al. |

Primary Examiner—Taofiq Solola
(74) Attorney, Agent, or Firm—Andrew J. Caruso; Patrick K. Patnode

(57) ABSTRACT

Oxydiphthalic anhydrides such as 4-oxydiphthalic anhydride are prepared by the reaction of a halophthalic anhydride with an alkali metal carbonate such as potassium carbonate. The reaction proceeds in the presence of a hexaalkylguaninium halide or α,ω-bis(pentaalkylguanidinium)alkane halide as a phase transfer catalyst.

15 Claims, No Drawings

METHOD FOR PREPARING OXYDIPHTHALIC ANHYDRIDES USING GUANIDINIUM SALT AS CATALYST

BACKGROUND OF THE INVENTION

This invention relates to the preparation of oxydiphthalic anhydrides, and more particularly to improved phase transfer catalyzed methods for such preparation.

Oxydiphthalic anhydrides, particularly 4,4'-oxydiphthalic anhydride, are important monomers for the preparation of polyetherimides having exceptionally high temperature performance and excellent solvent resistance. These properties are useful in high performance plastics applications such as advanced composites and electronic circuit materials.

A number of publications, chiefly of Occidental Chemical Corporation, describe the preparation of oxydiphthalic anhydrides by the reaction of halophthalic anhydrides with potassium carbonate. Such publications include U.S. Pat. Nos. 4,870,194, 5,021,168 and 5,153,335. Suitable reaction conditions include neat and solvent reactions and the presence of various catalysts, typically phase transfer catalysts such as tetraphenylphosphonium halides, fluorides such as potassium fluoride and cesium fluoride and carboxylic acids and their salts and hydrolysable esters. Many of these catalytic materials are relatively expensive or limited in their effectiveness, and product yields are often undesirably low. Moreover, numerous ambiguities are present in said publications regarding water content of the reaction mixtures and other conditions, making reproducibility questionable.

It is of interest, therefore, to provide a method for oxydiphthalic anhydride preparation which affords high yields and a minimum of by-products, and which is consistently and reproducibly applicable.

SUMMARY OF THE INVENTION

The present invention enables the preparation of oxydiphthalic anhydrides with the use of readily available and relatively inexpensive catalytic materials. Said preparation consistently affords high yields of the desired product and is highly reproducible.

In one embodiment the invention is a method for preparing an oxydiphthalic anhydride which comprises contacting, under reactive and substantially anhydrous conditions, at least one halophthalic anhydride with at least one carbonate of the formula $M_2CO_3$, wherein M is an alkali metal having an atomic number of at least 19, in the presence of a catalytic proportion of at least one phase transfer catalyst selected from the group consisting of hexaalkylguanidinium halides and α,ω-bis(pentaalkylguanidinium)alkane halides.

DETAILED DESCRIPTION PREFERRED EMBODIMENTS

The oxydiphthalic anhydrides that may be prepared by the method of the invention include 4,4'-oxydiphthalic (hereinafter sometimes designated "4-ODPA"), 3,3'-oxydiphthalic and 3,4'-oxydiphthalic anhydrides. The organic reagents for these compounds are, respectively, 4-halophthalic, 3-halophthalic and a mixture of 3- and 4-halophthalic anhydrides. For commercial purposes, the preferred anhydride is generally 4-ODPA, and frequent reference to it will be made hereinafter; it should be understood, however, that one of the other isomers may be substituted for 4-ODPA where appropriate.

Any halogen may be present in the halophthalic anhydride. Most often the fluoro-, chloro- or bromophthalic anhydride is employed, with the chlorophthalic anhydride being preferred by reason of its relatively low cost and particular suitability.

The reaction producing 4-ODPA is effected through the use of at least one carbonate of the formula $M_2CO_3$, in which M is an alkali metal such as sodium, potassium, rubidium or cesium. Mixtures of such carbonates may be employed. For optimum product yield, it is preferred to employ carbonates of alkali metals having an atomic number of at least about 19. Potassium carbonate is preferred.

Particle size of the carbonate can have an effect on product yield. Thus, powdered potassium carbonate has been shown to produce a higher yield of oxydiphthalic anhydride than granular potassium carbonate in the same time period. However, it has been found that powdered potassium carbonate is more difficult to dry than the granular form. By reason of the deleterious effect of water on the reaction, it is important if powdered potassium carbonate is used that it first be thoroughly dehydrated.

Contact between the halophthalic anhydride and the carbonate is under reactive conditions, generally including temperatures in the range of about 120–250° C. and preferably about 170–250° C., atmospheric pressure and a molar ratio of halophthalic anhydride to carbonate in the range of 1.4–3.0:1, preferably 2.04–2.22:1. Optimum theoretical yields require a molar ratio of 2:1, but it has been discovered that a side reaction producing the corresponding hydroxyphthalic anhydride can occur under some conditions at a substantial reaction rate if the molar ratio is 2:1 or lower. In the preferred range of 2.04–2.22:1, the rate of the side reaction is negligible and optimum conditions for obtaining the desired product in high yield are attained.

The reaction may be performed in the absence or in the presence of at least one solvent. In various embodiments it is preferred that the reaction be conducted in a solvent. While dipolar aprotic solvents may be used, their use is generally not advisable since they can promote side reactions and the formation of colored by-products. In various embodiments suitable solvents have a boiling point above about 120° C., preferably above about 150° C. and more preferably above about 180° C. Suitable solvents of this type include, but are not limited to, orthodichlorobenzene, para-dichlorobenzene, dichlorotoluene, 1,2,4-trichlorobenzene, diphenyl sulfone, phenetole, anisole and veratrole, and mixtures thereof. It is more preferred that chlorinated aromatic liquids be employed as solvents, examples of which include, but are not limited to, o-dichlorobenzene, 2,4-dichlorotoluene and 1,2,4-trichlorobenzene. 2,4-Dichlorotoluene is often most preferred since its use minimizes reaction time and product decomposition. In the case of some solvents, such as o-dichlorobenzene, the proportion of phase transfer catalyst can be increased and/or the reaction can be run at superatmospheric pressure to permit higher temperatures and higher reaction rates.

The reaction mixture should be substantially anhydrous, the term "substantially anhydrous" denoting a total water content of less than about 50, preferably less than about 20 and most preferably less than about 10 ppm by weight. Any water present above this amount can inhibit the reaction, irrespective of its source. Traces of water may be present in either of the reagents and also in the bicarbonate, and they should be carefully removed by drying before beginning the reaction. Drying can be achieved by methods known in the art. Liquid reagents and solvents can be dried by distillation and/or by contact with molecular sieves, and solid materials such as the carbonate and bicarbonate by heating in an oven, most often under vacuum.

In this connection, it should be noted that the present invention differs significantly from the reaction disclosed in the aforementioned U.S. Pat. No. 5,153,335. That patent is inconsistent as to the proportion of water present in the reaction mixture. Claim 1 requires a substantially anhydrous medium, but the specification states that the water content is in the range of 0.05–0.5 mole percent, supposedly corresponding to a weight proportion in the range of 100–2,000 ppm. By calculation, however, 100–2,000 ppm is equivalent to 0.2–4.0 mole percent. Thus, it is very difficult to draw any conclusions about the amount of water preferred according to the patent, or even whether the presence of water is contemplated.

In one embodiment of the present invention, a hexaalkylguanidinium halide or an α,ω-bis(pentaalkylguanidinium) alkane halide is used as a phase transfer catalyst. Such phase transfer catalysts are known in the art; reference is made, for example, to U.S. Pat. No. 5,229,482. Hexaalkylguanidinium halides are generally preferred, with hexaethylguanidinium halides being more preferred and hexaethylguanidinium chloride most preferred. It has been found that when a guanidinium salt is employed as a catalyst, the reaction is faster than when a phosphonium salt is employed, yielding an equivalent yield in a substantially shorter time.

The proportion of guanidinium salt employed is usually in the range of about 0.2–10.0, preferably about 1–3, mole percent based on halophthalic anhydride. For optimum yield with minimum product decomposition over time, the most preferred proportion is in the range of about 1.5–2.5 mole percent.

When the reaction between halophthalic anhydride and carbonate is complete, the product may be isolated by conventional techniques. It is often convenient to merely cool the solution in solvent after filtration while hot, whereupon the desired oxydiphthalic anhydride precipitates and may be removed by filtration.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

All parts and percentages are by weight unless otherwise designated. Chemicals and solvents were reagent grade, and were carefully dried and otherwise used without purification. Solvents were dried over activated 3Å molecular sieves before use. Granular or powdered potassium carbonate was dried in a vacuum oven overnight before use. Analysis was performed by contacting the reaction mixture with n-butylamine and acetic acid to convert anhydrides to the corresponding N-(n-butyl)imides, followed by high pressure liquid chromatography using a tetrahydrofuran-water mixture as the eluting solvent.

EXAMPLE 1

4-Chlorophthalic anhydride, 16 grams (g) (87.7 mmol), was weighed into a 150 milliliter (ml) three-necked flask fitted with a distillation head and containing about 100 ml of distilled o-dichlorobenzene having a water content of less than 5 ppm. The mixture was heated at reflux for 0.5 hour in a nitrogen atmosphere and about 80 ml of o-dichlorobenzene was removed by distillation.

Powdered potassium carbonate, 6.06 g (43.8 mmol), was added to another flask with 50 ml of dry o-dichlorobenzene. The suspension was heated at reflux for 0.5 hour under nitrogen and 40 ml of o-dichlorobenzene was distilled. The 4-chlorophthalic anhydride solution was transferred to the flask containing carbonate. The mixture was stirred and 468 mg (1.77 mmol) of hexaethylguanidinium chloride (in the form of an 18% solution in o-dichlorobenzene containing less than 15 ppm of water) was added, whereupon the solution turned yellow as refluxing was continued. Periodic analysis of the mixture showed a 93% yield of the desired 4,4'-ODPA after 3 hours. In a control experiment employing tetraphenylphosphonium bromide at the same mole percent level and powdered potassium carbonate, a period of 13 hours was required to attain the same yield.

EXMAPLE 2

The procedure of Example 1 was repeated except that granular potassium carbonate was used and the level of hexaethylguanidinium chloride was 2.0 mole percent based on 4-chlorophthalic anhydride. Product formation leveled off after 3 hours at a minimum of about 85% total yield.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

What is claimed is:

1. A method for preparing an oxydiphthalic anhydride which comprises contacting, under reactive and substantially anhydrous conditions, at least one halophthalic anhydride with a carbonate of the formula $M_2CO_3$, wherein M is an alkali metal, in the presence of a catalytic proportion of at least one phase transfer catalyst selected from the group consisting of hexaalkylguanidinium halides and α,ω-bis (pentaalkylguanidinium)alkane halides.

2. The method according to claim 1 wherein the halophthalic anhydride is 3-chlorophthalic anhydride, 4-chlorophthalic anhydride or a mixture thereof.

3. The method according to claim 2 wherein the halophthalic anhydride is 4-chlorophthalic anhydride.

4. The method according to claim 1 wherein M has an atomic number of at least about 19.

5. The method according to claim 4 wherein M is potassium.

6. The method according to claim 5 wherein the carbonate is powdered.

7. The method according to claim 1 wherein a solvent is also present.

8. The method according to claim 7 wherein the solvent is at least one member selected from the group consisting of orthodichlorobenzene, para-dichlorobenzene, dichlorotoluene, 2,4-dichlorotoluene, 1,2,4-trichlorobenzene, diphenyl sulfone, phenetole, anisole and veratrole, and mixtures thereof.

9. The method according to claim 8 wherein the solvent is o-dichlorobenzene, 2,4-ichlorotoluene or 1,2,4-trichlorobenzene.

10. The method according to claim 1 wherein the phase transfer catalyst is a hexaalkylguanidinium halide.

11. The method according to claim 10 wherein the phase transfer catalyst is hexaethylguanidinium chloride.

12. The method according to claim 1 wherein a molar ratio of halophthalic anhydride to carbonate in the range of 1.43.0:1 is employed.

13. The method according to claim 1 wherein a proportion of phase transfer catalyst is in the range of 0.2–10.0 mole percent based on halophthalic anhydride is employed.

14. The method according to claim 1 wherein a temperature in the range of about 120–250° C. is employed.

15. A method for preparing 4-oxydiphthalic anhydride which comprises contacting, in a solvent with boiling point greater than about 150° C. under substantially anhydrous conditions and at a temperature in the range of about 120–250° C., 4-chlorophthalic anhydride with potassium carbonate in the presence of a catalytic proportion of hexaethylguanidinium chloride the molar ratio of 4-chlorophthalic anhydride to potassium carbonate being in the range of 2.04–2.22:1 and the proportion of phase transfer catalyst being in the range of 1–3 mole percent based on 4-chlorophthalic anhydride.

\* \* \* \* \*